United States Patent
Budde et al.

(10) Patent No.: US 6,652,782 B1
(45) Date of Patent: Nov. 25, 2003

(54) MULTI-STAGE METHOD FOR PRODUCING GAS-FILLED MICROCAPSULES

(75) Inventors: Uwe Budde, Wandlitz (DE); Andreas Briel, Berlin (DE); Georg Rossling, Glienicke (DE); Kai Lovis, Berlin (DE); Wolfgang Schmidt, Berlin (DE); Hans-Ulrich Moritz, Bendestorf (DE); Michael Gottfried, Hamburg (DE); Jan-Peter Ingwersen, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/979,554

(22) PCT Filed: May 23, 2000

(86) PCT No.: PCT/DE00/01678

§ 371 (c)(1),
(2), (4) Date: Mar. 27, 2002

(87) PCT Pub. No.: WO00/72888

PCT Pub. Date: Dec. 7, 2000

(30) Foreign Application Priority Data

May 27, 1999 (DE) .......................................... 199 25 311

(51) Int. Cl.[7] .......................... B01J 13/02; B32B 15/02
(52) U.S. Cl. ......................... 264/4.4; 526/64; 526/65; 526/71; 526/72; 428/402.2; 428/402.21; 428/402.22; 264/4.7
(58) Field of Search ............................... 526/64, 65, 71, 526/72; 428/402.2, 402.21, 402.22; 264/4.4, 4.7

(56) References Cited

U.S. PATENT DOCUMENTS 5,501,863 A    3/1996   Rössling et al.

FOREIGN PATENT DOCUMENTS

| DE | 40 04 430 A | 8/1991 |
|---|---|---|
| DE | 42 19 723 A | 12/1993 |
| DE | 42 19 724 A | 12/1993 |
| DE | 44 03 789 A | 8/1995 |
| DE | 196 48 663 A | 5/1998 |
| WO | WO 94 07539 A | 4/1994 |
| WO | WO 95 07072 A | 3/1995 |

OTHER PUBLICATIONS

P. Sommerfeld et al., "Long–Term Stability of PBCA Nanoparticle Suspensions," Journal of Microencapsulation, vol. 17 No. 1, pp. 69–79, Jan.–Feb. 2000, XP0002150487.

P. Sommerfeld et al., "Long–Term Stability of PBCA Nanoparticle Suspensions Suggests Clinical Usefulness," International Journal of Pharmaceutics, vol. 155, No. 2, pp. 201–207, Sep. 26, 1997, NL. Amsterdam, XP002066668.

S.J. Douglas et al., "Biodistribution of Poly(Butyl 2–Cyanoacrylate) Nanoparticles in Rabbits," International Journal of Pharmaceutics, vol. 34, pp. 145–152, Amsterdam, NL, XP000946109, 1986.

J.R. Harris et al., "The Structure of Gas–Filled n–Butyl–2–cyanoacrylate (BCA) Polymer Particles," Micron, vol. 26, No. 2, pp. 103–111, 1995, XP000952692.

M.A. Vandelli et al., "Release Behaviour Of Polyethyl–and Polyisobutylcyanoacrylate Nanoparticles As A Function of Surfactant used in the Preparation Procedure," Bollettino Chimico Farmaceutico, vol. 132, No. 10, pp. 428–431, 1993, XP000952689.

S.J. Douglas et al., "Poly(butyl 2–cyanoacrylate) Nanoparticles With Differing Surface Charges," Journal of Controlled Release, vol. 3, No. 1, pp. 15–23, 1986, XP002150486.

*Primary Examiner*—Samuel A. Acquah
(74) *Attorney, Agent, or Firm*—Millen, White, Zelano & Branigan, P.C.

(57) ABSTRACT

The invention relates to a multi-stage method for producing gas-filled microcapsules. In one stage of the method, the substance that forms the coat is polymerized. The microcapsules are formed in a physically and/or temporally separate stage, by means of a structuring process. The polymerization is carried out with moderate stirring, while the microcapsules are structured in dispersing conditions.

38 Claims, No Drawings

MULTI-STAGE METHOD FOR PRODUCING GAS-FILLED MICROCAPSULES

The invention relates to a multi-stage process for the production of gas-filled microcapsules, in which the process steps of polymerization of the encasing substance and build-up of the microcapsule are carried out separately. The microcapsules that-are produced with the process according to the invention have a core-shell structure and are distinguished by a defined size distribution. Based on their properties, they can be used for ultrasound as contrast media that can pass capillaries.

The application is based on the following definitions:

A microcapsule is a particle that measures several $\mu$m and that consists of a gaseous core and a solid shell with variable thickness. The core can also contain a small proportion of liquid, in which the production is carried out.

Stirring is the mixing of a liquid with a liquid, solid or gaseous substance in such a way that the gas-phase proportion in the stirring medium is <1%.

Dispersing is the mixing of a liquid with a liquid, solid or gaseous substance in such a way that the gas-phase proportion in the dispersing medium is >1%, preferably greater than 10%.

Dispersion is a colloidal (particle size<500 nm) or coarsely dispersed (particle size>500 nm) multi-phase system.

Primary dispersion is a colloidal dispersion that consists of polymer particles, produced by polymerization of a monomer.

Self-gassing is the input of gas into a liquid by the movement of the gas or by the production of a dynamic flow underpressure.

External gassing is the active input of gas into a liquid.

Flotation is the movement of microparticles directed against the acceleration force (acceleration due to gravity g, radial acceleration a) based on a difference in density between microparticles and dispersing agents.

Floated material is the creamed layer of gas-filled microparticles after flotation.

Hydraulically filled is the same as completely filled without gas supernatant.

In the case of echocardiography (also: cardiac sonography), conclusions can be drawn on morphology and sequences of movements of cardiac valves as well as the direction, rate and quality of the circulation. In this process of diagnosis, the procedure is done with ultrasound, whose interactions are shown color-coded (Doppler process). Because of their complication-free, simple application, ultrasonic diagnosis has found wide use in medicine.

The quality of the results is considerably improved by the use of contrast media.

As contrast media, substances that contain or release gases are used in medical ultrasonic diagnosis as a rule, since a more efficient density and thus impedance difference than between liquids or solids and blood can be produced with them.

The observation of cardiac echo effects with solutions that contain finely dispersed gas bubbles have been known in the literature for a long time [1]. Since these unstabilized gas bubbles have only a very short service life, solutions that are produced in this way are unsuitable as contrast media for medical ultrasonic diagnosis.

In U.S. Pat. No. 4,276,885, a process for the production of gas bubbles, which are protected by a gelatin membrane before running together [2], is described. These microbubbles are preferably produced by an injection of the desired gas into a substance that can gel (for example gelatin) using a capillary. Storage of these microbubbles is possible only at low temperatures, whereby the latter are to be brought to body temperature again before in-vivo use. Heat-sterilization is excluded in principle, since in this case the microbubbles are destroyed just as in sterile filtration.

In European Patent EP 0 052 575 B1, ultrasonic contrast media that are based on physiologically well-tolerated solid aggregates that release gas bubbles into the blood stream after administration [3] are described. The released gas bubbles are not stabilized and do not survive passage through the lungs, so that after intravenous administration, only a contrasting of the right half of the heart is possible.

In Patents EP 0 122 624 and EP 0 123 235, ultrasonic contrast media that consist of microparticles and gas bubbles are described [4, 5]. In contrast to EP 0 052 575 B1, a stabilization of the gas bubbles is carried out by means of a surface-active substance. Passage through the lungs is possible, so that these contrast media allow a contrasting of the entire vascular volume.

Both production processes are very expensive, however.

According to European Patent EP 0 324 938 B1, encapsulated microbubbles can be produced by microbubbles being produced by ultrasound in a protein solution, which are subsequently stabilized in that because of a local temperature increase, the protein is partially denatured and the gas bubbles included [6].

The proposed use of human serum albumin (HSA) involves a considerable allergenic risk, however.

In European Patent EP 0 398 935 B1, microparticles whose shell substance consists of synthetic, biodegradable polymer material are described as ultrasonic contrast media. As a shell substance, in this case, a whole series of polymers are suitable, which are dissolved in a water-immiscible solvent or solvent mixture and are emulsified in water after possible addition of other solvents. As solvents, according to [7], furan, pentane and acetone can be used in addition to others. In a process variant, the monomer that is dissolved in one of the above-mentioned solvents is polymerized immediately in an aqueous solution that contains gas bubbles.

In all processes that are mentioned in the claims, the obligatory use of an organic solvent is of considerable disadvantage, since the latter has to be removed completely during the course of the production process.

With the techniques that are disclosed in European Patent EP 0 458 745, gas-filled microballoons can be produced in a wide range of sizes [8]. To this end, first a solution of the shaping polymer is emulsified in an organic solvent in water and then diluted, by which the finely dispersed polymer solution drops are solidified. The enclosed solvent must be removed in an additional step, which is an expensive process. It is advantageous in this process that there is a direct possible way of influencing the size of the microcapsules that are produced by the selection of the surfactant or the rpm. In this case, however, different forms of administration, such as the intravenous injection, which requires in particular small particles for passing through the lungs, as well as the oral administration with correspondingly larger particles, are to be covered by the process. A solvent-free synthesis of gas-filled microparticles is also not possible in this way, however.

A spray-drying process for the production of echogenic microparticles, of which concave surface segments are the first and foremost characteristic, is disclosed in European Patent EP 0 535 387 B1 [9]. In addition, the synthesis of various shell polymers with use of organic solvent is described. The echogenic microparticles are obtained by a spray-drying process of an organic solution of the shaping polymer. Disadvantageous in this process is also the use of organic solvents and the spray-drying process that is expensive under sterile conditions.

By process optimization, which is described in European Patent EP 0 644 777 B1, the ultrasonic activity of the microcapsules that are described in EP 0 327 490 could be significantly improved [10]. An increase of the ultrasonic activity (with specific frequency and smaller amplitude) is achieved by the diameter of the air core having been enlarged in the case of constant particle diameter. Despite the smaller wall thickness that results therefrom, the particles nevertheless survive passing through the cardiopulmonary system.

The optimized process is characterized in that the monomer is dispersed and polymerized in an acidic, gas-saturated, aqueous solution, and in this case the build-up of the microcapsule is carried out immediately. In this way, microcapsules can be produced without being dependent on organic solvents during the production process.

Difficulties arise in this process, however, during scale-up from the laboratory scale to the production scale, since the input of energy into the reaction medium depends to a considerable extent on the rpm and the diameter of the stirring or dispersing element. Consequently, it can be expected that the sensible ratios for the input of energy and air cannot easily be scaled up locally at the dispersing tool or the shear gradient within the reactor. By the large amount of air introduced at the dispersing tool, a considerable formation of foam can be observed, so that it is not possible to make adequate statements regarding the extent to which polymerization of the monomer and shell formation are carried out in a way according to requirements.

The object of the invention is to find a production process for echogenic microcapsules that does not have any of the above-mentioned drawbacks, i.e., The production of microcapsules must also be simple and reproducible under sterile conditions, the synthesis of the polymer and the microcapsule production must be feasible without organic solvents, scaling-up must be possible while retaining process control, and process monitoring must be easy, the microcapsules that can be produced with the process are to have an optimally adapted property profile as ultrasonic contrast media (defined size or size distribution, qualitatively and quantitatively reproducible ultrasonic contrasts), the microcapsules should have a high shelf life even under critical climactic conditions.

This object is achieved by this invention.

It has been found that not only nascent primarily latex particles form microcapsules during the polymerization process, but can also, surprisingly enough, cause microcapsule formation with completely polymerized or pre-polymerized polymer dispersions by suitable process control.

This production option makes it possible to break the comparatively complicated overall production process down into smaller steps. Thus, the overall production process is subject to a better control.

The subject of the invention therefore relates to a multi-stage process for the production of gas-filled microcapsules, in which a polymerization of the shell-forming substance is carried out in a first process step, and, separated in space and/or time from this first process step, a structuring process step for the formation of the microcapsules is carried out. The partial processes of polymerization and microcapsule formation are thus carried out separately.

The polymerization of the monomer is carried out here in aqueous, often acidic solution under stirring conditions such that the gas phase proportion in the stirring medium is <1%. These are generally moderate conditions that are characterized in an open reactor by an input of energy of less than 5 W/dm$^3$ and a Reynolds number (Re=n·d$^2$/v) of less than 50,000. If the polymerization is carried out in a closed system that is, for example, hydraulically filled, a polymerization according to requirements can also be performed at considerably different operating points.

In any case, vortex formation can be detected, if only to a slight extent.

As an intermediate product of this process step, a primary dispersion that consists of colloidal polymer particles is obtained.

The build-up of the microcapsule from this primary polymer dispersion is carried out under dispersing conditions in such a way that the gas phase proportion is >1%, preferably greater than 10%. These are generally conditions that are characterized by a large input of energy of more than 5 W/dm$^3$ and a Reynolds number (Re=n·d$^2$/v) of greater than 50,000. A vortex formation is readily evident. A directed structuring aggregation of the colloidal polymer particles is carried out in this process step.

The significant process improvement in the production of microcapsules lies in the fact that each individual partial step can be performed under the optimal process conditions in each case, such as, for example, temperature, pH, shear effects, etc.

The option thus exists of first producing a primary dispersion of the shell polymer that is optimally suitable for the formation of microcapsules to then produce the latter in another process step after setting the optimal conditions for the formation of microcapsules. This can advantageously be carried out immediately following polymerization.

As monomers, lactides, alkyl esters of acrylic acid, alkyl esters of methacrylic acid and preferably alkyl esters of cyanoacrylic acid can be used.

Especially preferred are butyl, ethyl and isopropylcyanoacrylic acid.

The stirring or dispersing medium can contain one or more of the following surfactants:

Alkylarylpoly(oxyethylene)sulfate alkali salts, dextrans, poly(oxyethylenes), poly(oxypropylene)-poly(oxyethylene)-block polymers, ethoxylated fatty alcohols (cetomacrogols), ethoxylated fatty acids, alkylphenolpoly(oxyethylenes), copolymers of alkylphenolpoly(oxyethylene) and aldehydes, partial fatty acid esters of sorbitan, partial fatty acid esters of poly(oxyethylene)sorbitan, fatty acid esters of poly(oxyethylene), fatty alcohol ethers of poly(oxyethylene), fatty acid esters of saccharose or macrogol glycerol esters, polyvinyl alcohols, poly(oxyethylene)-hydroxy fatty acid esters, macrogols of multivalent alcohols, partial fatty acid esters.

One or more of the following surfactants are preferably used: ethoxylated nonylphenols, ethoxylated octylphenols, copolymers of aldehydes and octylphenolpoly(oxyethylene), ethoxylated glycerol-partial fatty acid esters, ethoxylated hydrogenated castor oil, poly(oxyethylene)-hydroxystearate, poly(oxypropylene)-poly(oxyethylene)-block polymers with a molecular weight of <20,000.

Especially preferred surfactants are:

Para-octylphenol-poly-(oxyethylene) with 9–10 ethoxy groups on average (=octoxynol 9,10), paranonylphenol-poly(oxyethylene) with 30/40 ethoxy groups on average (=e.g., Emulan® 30/Emulan® 40), para-nonylphenol-poly(oxyethylene)-sulfate-Na salt with 28 ethoxy groups on average (=e.g., Disponil® AES), poly(oxyethylene)glycerol monostearate (e.g., Tagat® S), polyvinyl alcohol with a degree of polymerization of 600–700 and a degree of hydrolysis of 85%–90% (=e.g., Mowiol® 4-88), poly(oxyethylene)-660-hydroxystearic acid ester (=e.g., Solutol® HS 15), copolymer of formaldehyde and para-octylphenolpoly (oxyethylene) (=e.g., Triton® WR 1339), polyoxypropylene-polyoxyethylene-block polymers with a molecular weight of about 12,000 and a polyoxyethylene proportion of about 70% (=e.g., Lutrol® F127), ethoxylated cetylstearyl alcohol (=e.g., Cremophor® A25), ethoxylated castor oil (=e.g., Cremophor® EL).

In general, the production of the gas-filled microcapsules can be carried out in continuous, semi-continuous or batch operation. For polymerization, a combination of one or more identical or different reactors of the type of a stirring vessel, a flow pipe or a loop reactor is used for thorough mixing with suitable precautions.

For the production of gas-filled microcapsules, the reactor that is used has a suitable dispersing unit and the option of allowing a corresponding admission of gas into the reaction medium.

In the preferred process variant, a monomer from the group of the cyanoacrylic acid alkyl ester in an acidic, aqueous solution is added in drops in the process step of the polymerization. The addition is carried out under moderate stirring conditions, such that no self-gassing is carried out.

As a discontinuous reactor, especially a stirring vessel with a ratio of diameter to height in a range from 0.3 to 2.5, which is equipped with a temper jacket, is suitable.

The thorough mixing is preferably carried out with a stirring element, which has a ratio of stirrer to reactor diameter in a range of 0.2 to 0.7.

As stirring elements, in principle all commonly used stirrers are considered, but especially those that are used for the thorough mixing of low-viscous, water-like media (<10 mPas). These include, for example, propeller stirrers, vane stirrers, pitched-blade stirrers, MIG® stirrers and disk stirrers, etc. The insertion position can be, e.g., vertically in the direction of the normal of the liquid surface of the reaction medium, in oblique form against the normal or laterally through the container walls. The latter option arises in the case of a container that is filled completely gas-free and externally encapsulated against the atmosphere.

The use of flow-breakers is also possible. In this connection, it is ensured that the tendency toward self-gassing in an open system is especially low in the production of the primary dispersion.

Degassing of the reaction media can, but does not have to, take place. The reaction media usually have the temperature-dependent gas content of the gas (of the gases) of the surrounding atmosphere. As a whole, the production should be carried out so that no optically detectable increase of the volume of the reaction medium is carried out by the input of gas ($\Phi_G$<<1%).

The type of dosage in connection with the other internals that contribute to thorough mixing, the stirrer and the rpm also should be selected such that the mixing time in comparison to the reaction period of the polymerization process is very small to ensure the quickest possible micromixing of the monomer in the acidic, aqueous solution.

By the comparatively readily understood hydrodynamics of a discontinuous stirring vessel, there are not significant difficulties in the case of scaling-up from the laboratory scale to the industrial scale or the production scale, which has to be evaluated as advantageous for the commercial application of this process.

When done properly, no foam is observed to form. During polymerization, only very little or no input of gas is carried out, and cavitation effects are excluded because of moderate stirring conditions. It is very readily possible, by using suitable on-line process probes (e.g., IR, NIR or Raman probes for conversion), which are often of no use in strongly foaming reaction media, to structure reaction and process control in a safe manner.

It is also possible, after the reaction ends, to test the polymer dispersion and conventionally to perform off-line analysis. Thus, e.g., the mean particle size and distribution can then be determined.

The feed of monomers during semi-continuous polymerization represents another, also successfully performed technique for setting desired particle size distributions, so that the growth of a particle population that is generated in the initial phase of the polymerization is influenced specifically.

The polymerization is performed at temperatures of −10° C. to 60° C., preferably in a range of 0° C. to 50° C. and especially preferably between 10° C. and 35° C.

Setting the reaction speed of the polymerization of the cyanoacrylic acid ester and the mean particle size that results therefrom is carried out, i.a., in addition to the temperature, via the pH that can be set based on acid and concentration in a range of 1.0 to 4.5, for example by acids, such as hydrochloric acid, phosphoric acid and/or sulfuric acid. Other values of influence on the reaction speed are the type and concentration of the surfactant and the type and concentration of additives.

The monomer is added at a concentration of 0.1 to 60%, preferably 0.1 to 10%, to the aqueous, mostly acidic, solution.

In an implementation according to the above-mentioned conditions, the polymerization time is between 2 minutes and 2 hours and can be tracked, i.a., by reaction-calorimetry. This wide range of the reaction time is a result of the flexible variation options in the selection of the process parameters, in which the particle size as well as the particle size distribution of the polymer latex particles that are produced can be controlled. The latter are the central values of influence in the subsequent formation of the gas-filled microcapsules, which thus can be influenced in a positive manner by the selection of suitable polymerization parameters.

The diameter of the polymer latex particles that are produced according to this formulation for the encapsulation of gas lies in a range of 10 nm to 500 nm, preferably in a range of 30 nm to 150 nm, especially advantageously in a range of 60 nm to 120 nm. The thus produced polymer particles have a controllable size distribution with a polydispersity down to a range of 1.4 to 1.0 ($d_w/d_n$).

There are no sterility problems in this simple reaction structuring. For the aseptic fabrication of microcapsules, it is possible to subject this polymerization dispersion to a sterile filtration, such that the aseptic fabrication process can be carried out simply.

Following the polymerization, as a further advantage of this multi-stage process, a large proportion that is optionally produced during polymerization can be separated (e.g., by filtration), such that the latter no longer has a disturbing effect on the formation process of the microcapsules.

In addition to other process steps, such as the already mentioned filtration, dialysis is also possible. Thus, the surfactant content of the primary dispersion can be reduced again. The surfactant can then be replaced completely or partially by another for the next step, the build-up process of completely polymerized latex particles into microcapsules. In addition, other adjuvants can be added.

The formation of the gas-filled microcapsules is carried out in another step by structure-building aggregation of the colloidal polymer particles. This process step is carried out separated in space and/or time from the production of the primary dispersion.

To this end, the primary dispersion must be stirred with a dispersing tool, such that the phase proportion of gas $\Phi_G$ in the reaction mixture increases to values significantly above 1%, generally more than 10%. The gas phase proportion in the medium often is even more than 50%. Thus, a correspondingly large increase of the volume is associated with the reaction mixture. An intensive formation of foam is carried out, which can be quantified via a transmission measurement by a cloudiness sensor. With high-speed dispersion, the gas chamber around the vortex that is produced is sufficient for the production of gas-filled microcapsules.

The build-up of the microcapsule is performed at temperatures of −10° C. to 60° C., preferably at a range of 0° C. to 50° C. and especially preferably between 10° C. and 35° C.

The size and the size distribution of these microcapsules are determined by various process parameters, for example the shear gradient or the stirring period. The diameter of the gas-filled microcapsules is in a range of 0.2–50 $\mu$m, in the case of preparations for parenteral use preferably between 0.5 and 10 $\mu$m and especially preferably between 0.5 and 3 $\mu$m.

As dispersing tools in the production of gas-filled microcapsules, especially rotor-stator-mixers that can produce a high shear gradient are suitable. In addition, they ensure a large input of gas simultaneously to the time frame that is necessary for the production of microcapsules.

The dimensions and the operating sizes of the dispersing tool(s) essentially determine the particle size distributions of the microcapsules; their sizing also depends on the size and cooling capacity of the unit.

An advantageous option of the multi-stage process according to the invention consists in that it is not necessary to completely process a batch.

That is to say, the option exists of merging several different primary dispersions that can also contain, in each case, various polymers to build up gas-filled microcapsules therefrom.

A primary dispersion can also be divided into portions that each are then further built up into gas-filled microcapsules. In addition, necessary or optimally suitable adjuvants can be added to the process steps below.

After the formation of the microcapsules is completed, all options are open for further processing: e.g., the separation of gas-filled microcapsules based on the density difference in the liquid medium. With sufficiently pressure-stable microcapsules, centrifuging can be carried out, etc.

The property profile can be controlled especially readily by the organization of the production process into partial steps.

In scaling-up, there is also an improvement relative to the prior art. Since the processes of thorough mixing, polymerization and the build-up of microcapsules, coupled in a one-stage process, occur in parallel, these three processes must simultaneously be scaled-up. In the separation of the entire process into individual processes, it is advantageously exploited that focussing on the values that are important to the respective process is significantly simpler, because the process is broken down into sub-processes with fewer characteristic values.

For scaling-up, it is always true that it is impossible to maintain all dimensional ratios that describe the process such as heat exchange surface to reactor volume (A/V) or parameters such as diameter of the stirrer to diameter of the reactor ($d_{stirrer}/d_{reactor}$) gas phase content ($\Phi_G$) Reynolds number (Re), Nusselt number (Nu), Newton's number (Ne), Prandtl number (Pr), reactor level/reactor diameter (h/d), etc.

Parameters also emerge here that contain only material values, for example the Prandtl number, and that actually should not be affected by the scale-up. These material constants, however, which include, e.g., heat capacity, density, viscosity or the mean specific thermal conductivity of the reaction medium, are a function of relative gas phase content $\Phi_G$, such that all of these parameters in addition depend on the relative gas phase content.

In this connection, important values for the production of the primary dispersion and the build-up reaction of the microcapsules are in addition to the basic values, such as temperature, formulation, etc., of the gas phase proportion, the specific input of energy and the Reynolds number. The latter naturally assume different values for the two process steps. For the process step of the build-up of the microcapsule, especially the thermal control and the associated (parameters) values such as Nu ($\Phi_G$), A/V, heat-transfer coefficient ($\alpha$), Pr ($\Phi_G$) etc. are important because of the high specific input of energy. These considerations also apply for the possible process variants that are mentioned below.

A concrete process variant consists in performing the production of the primary dispersion in a continuous reactor, whereby to this end tube reactors with their tightly defined dwell-time behavior are more suitable than stirring vessel reactors. By the suitable selection of polymerization parameters, the reactor geometry and the mean dwell time can be ensured in a simple way in a tube reactor, such that the polymerization at the end of the tube reactor is fully completed. The option of on-line analysis exists just like in the batch reactor.

At the end of the tube reactor, a multi-stage rotor-stator system also can be used for the build-up reaction of microcapsules, so that the entire process is performed in a single apparatus, and the two process steps, the production of a polymer dispersion and the build-up reaction of microcapsules nevertheless are decoupled from one another.

Another process variant calls for the use of a loop reactor, which consists of a continuous stirring vessel or optionally an intermittent stirring vessel with an outside loop, which contains a one- or multi-stage inline dispersing unit or a one- or multi-stage rotor-stator system, which in addition can produce the output for the outside loop.

In this case, the production of the primary dispersion is carried out either in the stirring vessel area under moderate stirring conditions as well as in the closed loop or in the entire loop reactor when the loop is open, specifically under circulation conditions that do not allow any self-gassing by correspondingly adjusted speed ranges.

In this case, the process with the open loop offers the advantage of especially advantageously configuring the micromixing of the monomer in the aqueous solution by a directed dosage of the monomer in the feed area of the rotor-stator unit.

After the reaction ends, the loop is either opened to allow then the build-up reaction of the microcapsules by the rotor-stator unit that is integrated in the loop, or the speed range of the rotor-stator unit increases accordingly when the loop is open from the outset. During this process step, self-gassing in the stirring vessel area via a vortex or else an external gassing in the form of a directed dosage in the feed area of the rotor-stator unit can be performed. The last-mentioned process offers the advantage of a feed that can be controlled specifically.

With respect to the simplest possible scaling-up of the process for the production of microcapsules, all above-mentioned processes, which have a rotor-stator unit in the circulating pipe of a loop reactor or in the pipe portion of a continuous flow pipe, are preferable to pure stirring-vessel processes. A reason for this is that in increasing the stirring vessel volume or the volume to be produced, the in-line dispersing system does not necessarily have to be increased accordingly, but rather only the operating time has to be adapted. Another reason is evident in the fact that the dispersing action of a rotor-stator unit in a flushed pipe generally can be quantified more easily than in a stirring vessel reactor, by which the scaling-up is also clearly shown more advantageously.

After the two process steps are completed, the reaction batch can be worked up further.

The separation of gas-filled microcapsules from the reaction medium is advisable.

This can be done in a simple way with use of the density difference by flotation or centrifuging. In both cases, the gas-filled microcapsules form a floated material, which can be separated easily from the reaction medium.

The floated material that is obtained can then be taken up with a physiologically compatible vehicle, in the simplest case water or physiological common salt solution.

The suspension can be administered immediately. Dilution optionally is advisable.

The separation process can also be repeated one or more times. By directed setting of the flotation conditions, fractions with defined properties can be obtained.

The suspensions are stable over a very long period, and the microcapsules do not aggregate.

The durability can nevertheless be improved by subsequent freeze-drying optionally after the addition of polyvinylpyrrolidone, polyvinyl alcohol, gelatin, human serum albumin or another cryoprotector that is familiar to one skilled in the art.

The invention is explained by the following examples:

EXAMPLE 1

In a 1 l glass reactor with a diameter to height ratio of 0.5, 800 ml of water is set to a pH of 2.5 and a reactor temperature of 290.5 K by adding 0.1N hydrochloric acid. While being stirred moderately with a propeller stirrer to keep air from getting in, 8.0 g of octoxynol is added and stirred until the octoxynol is completely dissolved. Then, under the same stirring conditions over a period of 5 minutes, 11.20 g of cyanoacrylic acid butyl ester is added in drops, and the solution is stirred for another 30 minutes. After the polymerization is completed, the polymer dispersion is filtered to separate larger polymer particles. The filtered dispersion is mixed for 60 minutes with a rotor-stator mixer at high shear gradients. By the intensive mixing, self-gassing of the process medium is carried out with the result of a strong formation of foam. After the reaction ends, a framing layer of gas-filled microcapsules is formed.

The floated material is separated from the reaction medium and taken up with 600 ml of water for injection purposes. Then, 60 g of polyvinylpyrrolidone is dissolved in the batch, the suspension is formulated to 5 g and freeze-dried.

EXAMPLE 2

In a 2 l glass reactor with a diameter to height ratio of about 0.5 and an outside loop with a one-stage rotor-stator mixing unit, 1 l of a solution of 1% octoxynol is introduced at a pH of 2.5, and then 14 g of cyanoacrylic acid butyl ester is added in drops over 5 minutes, and the solution is stirred for 30 minutes to be introduced without air into the reaction mixture.

Then, the outside loop is attached to the circuit for 60 minutes. The stirrer in the glass reactor is set such that self-gassing of the reaction mixture is carried out. After the end of the test, a framing layer is formed.

The floated material is separated from the reaction medium and taken up with 1.5 l of water for injection purposes. Then, 150 g of polyvinylpyrrolidone is dissolved in the batch, the suspension is formulated up to 10 g and freeze-dried.

EXAMPLE 3

In a 50 l steel reactor with a diameter to height ratio of about 0.5 and an outside loop with a three-stage rotor-stator-mixed unit, 30 l of a solution of 1% octoxynol is introduced at a pH of 2.5. 430 g of cyanoacrylic acid butyl ester in the outside loop is added immediately before the rotor-stator mixing unit. In this case, the rotor-stator is operated such that no self-gassing of the medium is carried out. The solution is repumped for 30 minutes in the outside loop.

Then, an external gassing in the outside loop is carried out with air immediately before the high-speed running three-stage rotor-stator mixed unit. In this case, the solution is repumped for another 60 minutes in the outside loop. After the end of the test, a framing layer is formed.

The floated material is separated from the reaction medium and taken up with 35 l of water for injection purposes. Then, 3.5 kg of polyvinylpyrrolidone is dissolved in the batch, the suspension is formulated to 7.5 g and freeze-dried.

EXAMPLE 4

In a 1 l glass reactor with the diameter to height ratio of 0.5, 800 ml of water is set at a pH of 1.50 and a reactor temperature of 288 K by adding 0.1N hydrochloric acid. While being stirred moderately with a propeller stirrer to keep air from getting in, 8.0 g of an alkylaryl ether sulfate (Disponil AES 72) is added and stirred until the surfactant is completely dissolved. Then, under the same stirring conditions over a period of 5 minutes, 11.20 g of cyanoacrylic acid butyl ester is added in drops, and the solution is stirred for 30 minutes. After the polymerization is completed, the polymer dispersion is filtered to separate larger polymer particles.

The filtered dispersion is treated for 60 minutes with an Ultraturrax at high shear gradients (about 14,000 $s^{-1}$). By intensive mixing, an input of air into the process medium is automatically carried out with the result of a strong formation of foam. After the reaction ends, a framing layer of gas-filled microcapsules is formed.

The floated material is separated from the reaction medium and taken up in 600 ml of water for injection purposes. Then, 60 g of polyvinylpyrrolidone is dissolved in the batch, the suspension is formulated in amounts to 5 g and freeze-dried.

EXAMPLE 5

In a 1 l glass reactor with the diameter to height ratio of 0.5, 1,000 ml of water is set at a pH of 2.50 and a reactor temperature of 288 k by adding 0.1 N hydrochloric acid. While being stirred moderately with a propeller stirrer to keep air from getting in, 10.0 g of a polyvinyl alcohol (Mowiol 4-88) is added and stirred until the surfactant is completely dissolved. Then, under the same stirring conditions over a period of 5 minutes, 1.40 g of cyanoacrylic acid butyl ester is added in drops, and the solution is stirred for 45 minutes. After the polymerization is completed, the polymer dispersion is filtered to separate larger polymer particles.

The filtered dispersion is treated for 60 minutes with an Ultraturrax at high shear gradients (about 14,000 s$^{-1}$). By the intensive mixing, an input of air into the process medium is automatically carried out with the result of a strong formation of foam. After the reaction ends, a framing layer of gas-filled microcapsules is formed.

The floated material is separated from the reaction medium and taken up in 1,500 ml of water for injection purposes. Then, 150 g of polyvinyl pyrrolidone is dissolved in the batch, the suspension is formulated in amounts to 5 g and freeze-dried.

[1] J. ROELANDT Contrast Echocardiography (Review) Ultrasound Med. Biol. 8, pp. 471–492, 1982
[2] U.S. Pat. No. 4,276,885, May 4, 1979 E. G. TICKNER ET AL. Ultrasonic Image Enhancement Rasor Associates, Inc.
[3] European Patent EP 0 052 575, Nov. 17, 1980 J. S. RASOR, E. G. TICKNER Composition Generating Microbubbles Schering AG
[4] European Patent EP 0 122 624, Apr. 15, 1983 J. HILLMANN ET AL. Mikrokapsel und Gasbläschen enthaltendes Ultraschallkontrastmittel [Ultrasonic Contrast Media that Contain Microcapsules and Gas Bubbles] Schering AG
[5] European Patent EP 0 123 235, Apr. 15, 1983 J. HILLMANN ET AL. Mikrokapsel und Gasbläschen enthaltendes Ultraschallkontrastmittel Schering AG
[6] European Patent EP 0 324 938 B1, Dec. 29, 1987 K. J. WIDDER, P. J. WESTKAEMPER Concentrated Stabilized Microbubble-type Ultrasonic Imaging Agent and Method of Production Molecular Biosystems, Inc.
[7] European Patent EP 0 398 935 B1, Feb. 5, 1988 M. STEIN ET AL. Ultraschallkontrastmittel, Verfahren zu deren Herstellung und deren Verwendung als Diagnostika und Therapeutika [Ultrasonic Contrast Media, Process for their Production and their Use as Diagnostic Agents and Therapeutic Agents] Schering AG
[8] European Patent EP 0 458 749, May 18, 1990 D. BICHON ET AL. Mit Gas oder Luft gefüllte polymere Mikrokapseln, verwendbar in Form von Suspension bei flüssigen Trägern fur Ultraschall-Echographie [Polymer Microcapsules that are Filled with Gas or Air and That Can be Used in the Form of a Suspension with Liquid Vehicles for Ultrasonic Echography] Bracco Int.
[9] European Patent EP 0 535 387 B1, Sep. 3, 1990 V. KRONE ET AL. Echogene Partikel, Verfahren zu deren Herstellung und deren Verwendung [Echogenic Particles, Process for their Production and their Use] Hoechst AG
[10] European Patent EP 0 644 777 B1, Jun. 13, 1992 M. STEIN ET AL. Microparticles, method of producing them and their use for diagnostic purposes Schering AG

What is claimed is:

1. Multi-stage process for the production of gas-filled microcapsules, which comprises polymerizing one or more shell-forming monomers to form a dispersion comprising colloidal polymer particles and forming the microcapsules by aggregation of the colloidal polymer particles in the presence of a gas, wherein the polymerization of the one or more monomers is carried out in a first process step, and the formation of the microcapsules is carried out in a process step that is separated in space and/or time from the polymerization step.

2. Process according to claim 1, wherein the polymerization of the shell-forming monomer is in aqueous solution and is carried out under stirring conditions in a stirring medium such that the proportion of a gas phase in the stirring medium is <1%.

3. Process according to claim 1, wherein the forming of the microcapsules by aggregation of the colloidal polymer particles in the presence of a gas is carried out under dispersing conditions in a dispersing medium such that the gas phase proportion in the dispersing medium is >1%.

4. Process according to claim 1, wherein the polymerization of the one or more monomers is in an intermittent, semi-continuous or continuous stirring vessel with a diameter to height ratio of 0.3 to 2.5.

5. Process according to claim 1, wherein the polymerization of the one or more monomers is carried out in an intermittent, semi-continuous or continuous stirring vessel with a diameter to height ratio of 0.3 to 2.5, and is performed with an outside loop (loop reactor), in which a single-stage or multi-stage dispersing unit is arranged, and cut in at the beginning of the reaction or later.

6. Process according to claim 1, wherein the polymerization of the one or more monomers is performed with a vertical, oblique or lateral stirring element, whose diameter in ratio to the reactor diameter is in the range of 0.2 to 0.7.

7. Process according to claim 1, wherein the polymerization of the one or more monomers is performed in a continuously operated tubular-flow reactor.

8. Process according to claim 1, wherein the polymerization of the one or more monomers is performed in a hydraulically filled container that is externally encapsulated against the atmosphere.

9. Process according to claim 1, wherein the forming of the microcapsules by aggregation of the colloidal polymer particles is carried out with a dispersing unit.

10. Process according to claim 1, wherein the forming of the microcapsules by aggregation of the colloidal polymer particles is carried out with a rotor-stator system.

11. Process according to claim 1, wherein forming of the microcapsules by aggregation of the colloidal polymer particles is carried out with a rotor-stator system wherein the gas from self-gassing and/or introduced into the reaction mixture by external gassing.

12. Process according to claim 1, wherein the forming of the microcapsules by aggregation of the colloidal polymer particles is carried out with a rotor-stator system that is arranged in a stirring vessel with a diameter to height ratio of 0.3 to 2.5.

13. Process according to claim 1, wherein the forming of the microcapsules by aggregation of the colloidal polymer particles is carried out with a rotor-stator system, which is arranged in the outside loop of a loop reactor.

14. Process according to claim 1, wherein the one or more shell-forming monomers are one or more of the following monomers: lactides, alkyl esters of acrylic acid, alkyl esters of methacrylic acid, and alkyl esters of cyanoacrylic acid.

15. Process according to claim 1, wherein the one or more shell-forming monomers are one or more of the following monomers: butylcyanoacrylic acid, ethylcyanoacrylic acid and isopropylcyanoacrylic acid.

16. Process according to claim 1, wherein the polymerization of the one or more shell-forming monomers is conducted in an acidic aqueous solution wherein the monomers are in a concentration of 0.1 to 60%.

17. Process according to claim 1, wherein one or more of the following surfactants are used during polymerizing and/or during forming the microcapsules:

Alkylarylpoly(oxyethylene)sulfate alkali salts, dextrans, poly(oxyethylenes), poly(oxypropylene)-poly(oxyethylene)-block polymers, ethoxylated fatty alcohols (cetomacrogols), ethoxylated fatty acids, alkylphenolpoly(oxyethylenes), copolymers of alkylphenolpoly(oxyethylene) and aldehydes, partial fatty acid esters of sorbitan, partial fatty acid esters of poly(oxyethylene) sorbitan, fatty acid esters of poly(oxyethylene), fatty alcohol ethers of poly(oxyethylene), fatty acid esters of saccharose or macrogol glycerol esters, polyvinyl alcohols, poly(oxyetheylene)-hydroxy fatty acid esters, macrogols of multivalent alcohols, partial fatty acid esters.

18. Process according to claim 1, wherein one or more of the following surfactants are used during polymerizing and/or during forming the microcapsules:

Ethoxylated nonylphenols, ethoxylated octylphenols, copolymers of aldehydes and octylphenolpoly(oxyethylene), ethoxylated glycerol-partial fatty acid esters, ethoxylated hydrogenated castor oil, poly(oxyethylene)-hydroxystearate, poly(oxypropylene) poly(oxyethylene)-block polymers with a molecular weight of<20,000.

19. Process according to claim 1, wherein one of more of the following surfactants are used during polymerizing and/or during forming the microcapsules:

Para-octylphenol-poly-(oxyethylene) with 9–10 ethoxy groups on average, para-nonylphenol-poly(oxyethylene) with 30/40 ethoxy groups on average, para-nonylphenol-poly(oxyethylene)-sulfate-Na salt with 28 ethoxy groups on average, poly(oxyethylene) glycerol monostearate, polyvinyl alcohol with a degree of polymerization of 600–700 and a degree of hydrolysis of 85%–90%, poly(oxyethylene)-600-hydroxystearic acid ester, copolymer of formaldehyde and para-octylphenolpoly(oxyethylene), polyoxypropylenepolyoxyethylene-block polymers with a molecular weight of about 12,000 and a polyoxyethylene proportion of about 70%, ethoxylated cetylstearyl alcohol, ethoxylated castor oil.

20. Process according to claim 19, wherein the surfactant or surfactants are used at a concentration of 0.1 to 10%.

21. Process according to claim 1, wherein at least one of the process steps is performed in acidic, aqueous solution.

22. Process according to claim 21, wherein the following acid or acids are in the acidic, aqueous solution: hydrochloric acid, phosphoric acid and/or sulfuric acid.

23. Process according to claim 1, wherein the polymerization and the formation of the microcapsules are carried out at in a temperature range from −10° C. to 60° C.

24. Process according to claim 1, wherein the formed gas-filled microcapsules are separated, taken up in a physiologically compatible medium, and optionally are freeze-dried after a cryoprotector is added.

25. Process according to claim 24, wherein water or 0.9% common salt solution is the physiologically compatible medium.

26. Process according to claim 24, wherein polyvinylpyrrolidone, polyvinyl alcohol, gelatin and/or human serum albumin is used as a cryoprotector.

27. Microparticles, obtained according to the process of claim 1.

28. Process according to claim 1, wherein the forming the microcapsules by aggregation of the colloidal polymer particles in the presence of a gas is carried out under dispersing conditions in a dispersing medium such that the gas phase proportion in the dispersing medium is >10%.

29. Process according to claim 1, wherein the polymerization of the one or more shell-forming monomers is conducted in an acidic aqueous solution wherein the monomers are in a concentration of 0.1 to 10%.

30. Process according to claim 1, wherein the polymerization and the formation of the microcapsules are carried out at in a temperature range from 0° C. to 50° C.

31. Process according to claim 1, wherein the polymerization and the formation of the microcapsules are carried out at in a temperature range from 10° C. to 35° C.

32. Process according to claim 2, wherein the forming of the microcapsules by aggregation of the colloidal polymer particles in the presence of a gas is carried out under dispersing conditions in a dispersing medium such that the gas phase proportion in the dispersing medium is >1%.

33. Process according to claim 1, wherein the polymerization and the formation of the microcapsules are carried out in the absence of an organic solvent.

34. Process according to claim 1, wherein the step of polymerization and the step of formation of the microcapsules are carried out under conditions which differ as to temperature, pH and/or shear effects.

35. Process according to claim 1, wherein the gas-filled capsules produced have a diameter of from 0.2 to 50 μm.

36. Process according to claim 1, wherein the gas-filled capsules produced have a diameter of from 0.5 to 10 μm.

37. Process according to claim 1, wherein the gas-filled capsules produced have a diameter of from 0.5 to 3 μm.

38. Process according to claim 1, which further comprises a step of separating the colloidal polymer particles by filtration between the step of polymerization and the step of formation of the microcapsules.

* * * * *

UNITED STATES PATENT AND TRADEMARK OFFICE
CERTIFICATE OF CORRECTION

PATENT NO. : 6,652,782 B1
DATED : November 25, 2003
INVENTOR(S) : Uwe Buddle et al.

It is certified that error appears in the above-identified patent and that said Letters Patent is hereby corrected as shown below:

Column 12,
Line 44, reads "wherein forming" should read -- wherein the forming --
Line 47, reads "gas from" should read -- gas is from --

Column 13,
Line 26, reads "poly(oxypropylene)" should read -- poly(oxypropylene)- --
Line 40, reads "-600-" should read -- -660- --
Line 43, reads "polyoxypropylenepolyoxethylene-block" should read
-- polyoxypropylene-polyoxyethlene-block --

Column 14,
Line 13, reads "Microparticles" should read -- Microparticles --
Lines 43, 45 and 47, reads "capsules" should read -- microcapsules --

Signed and Sealed this

Twenty-fourth Day of August, 2004

JON W. DUDAS
*Director of the United States Patent and Trademark Office*